United States Patent [19]
Aleksejczyk et al.

[11] Patent Number: 5,385,750
[45] Date of Patent: Jan. 31, 1995

[54] ALKYL GLYCOSIDE COMPOSITIONS WITH IMPROVED WETTING PROPERTIES

[75] Inventors: Robert A. Aleksejczyk, Hatfield; Allen D. Urfer, Lansdale, both of Pa.

[73] Assignee: Henkel Corporation, Plymouth Meeting, Pa.

[21] Appl. No.: 883,000

[22] Filed: May 14, 1992

[51] Int. Cl.$^6$ ............................................. A01N 25/30
[52] U.S. Cl. ..................... 427/4; 106/15.05; 252/156
[58] Field of Search .......... 427/4; 106/15.05; 252/156

[56] References Cited

U.S. PATENT DOCUMENTS

| | | | |
|---|---|---|---|
| H224 | 3/1987 | Malik et al. | 71/92 |
| H303 | 7/1987 | Malik et al. | 514/85 |
| 3,199,944 | 8/1965 | Gabor et al. | 427/4 |
| 3,547,828 | 12/1970 | Mansfield et al. | 252/351 |
| 4,393,203 | 7/1983 | Mao et al. | 536/124 |
| 4,624,919 | 11/1986 | Kokusho et al. | 435/72 |
| 4,888,325 | 12/1989 | Schroeder et al. | 514/25 |
| 4,939,245 | 7/1990 | Rasche et al. | 536/18.6 |
| 5,104,658 | 4/1992 | Hagarty | 424/405 |
| 5,166,337 | 11/1992 | Ripke | 536/126 |

FOREIGN PATENT DOCUMENTS

| | | |
|---|---|---|
| 0220902 | 5/1987 | European Pat. Off. . |
| 364202 | 4/1990 | European Pat. Off. . |
| 388810 | 9/1990 | European Pat. Off. . |
| 1578753 | 8/1969 | France . |
| 3247050 | 6/1984 | Germany . |

OTHER PUBLICATIONS

Page et al, *The Insecticide, Herbicide, Fungicide, Quick Guide,* pp. 3-5, 57-59, 109-110; 1991 (no month available).

*Primary Examiner*—Shrive Beck
*Assistant Examiner*—Diana Dudash
*Attorney, Agent, or Firm*—Ernest G. Szoke; Wayne C. Jaeschke; Daniel S. Ortiz

[57] ABSTRACT

A method for improving the wetting ability of aqueous compositions used to coat substrates by including in the aqueous compositions a mixture of aliphatic glycoside and a fatty alcohol containing from 7 to 20 carbon atoms.

24 Claims, 6 Drawing Sheets

ALKYL GLYCOSIDE COMPOSITIONS WITH IMPROVED WETTING PROPERTIES

BACKGROUND OF THE INVENTION

At times it is desirable to provide a thin layer of a material on the surface of a substrate. This can be accomplished by providing a mixture of the material to be spread on the surface of the substrate with water. The spreading of the material is generally assisted by addition of a surfactant to the aqueous mixture to reduce the interfacial tension between the water and the substrate.

Application of aqueous agricultural pesticide formulations to plant materials and particularly food crop materials has special requirements. When the material to be spread on the substrate is an insoluble solid or an insoluble oily solid or liquid substance, a surfactant is generally added to the oily or insoluble material and water so that a suspension or emulsion can be formed.

Alkyl polyglycosides are known to be excellent surfactants for assisting in forming a mixture of water insoluble materials and water. In particular, organic polyglycosides are particularly useful as adjuvants for pesticidal materials (see U.S. Pat. No. 4,888,325, and Statutory Invention Registration H 303). However, the organic polyglycosides which are the most effective in forming mixtures of the water soluble materials and water are generally materials which have poor wetting characteristics. That is, the organic polyglycosides which have the most favorable characteristics for forming uniform mixtures and suspensions are not the most effective in reducing the interfacial tension between the mixture and the substrate to which it is applied.

BRIEF DESCRIPTION OF THE INVENTION

The wetting ability of an aqueous mixture containing an aliphatic polyglycoside and a material which is to be spread on the surface of a plant material, can be improved by including in the aqueous mixture of the aliphatic polyglycoside and the material to be spread on the plant material, a wetting improving amount of a fatty alcohol.

When the material is required to penetrate a biological material, the addition of the fatty alcohol can improve the rate of penetration particularly when the surface of the substrate comprises an oily or wax-like surface layer. The aliphatic polyglycoside with the added fatty alcohol more rapidly wets the surface of the plant and aids in penetration of the waxy or oily surface by the aqueous material spread on the surface.

Applicants have also discovered that aliphatic monoglycosides are particularly useful adjuvants in aqueous mixtures which must be spread on a leaf surface. The aliphatic monoglycosides are particularly effective in forming stable systems between organic materials and water. The monoglycosides also aid in assisting penetration of waxy layers. The aliphatic monoglycosides in conjunction with fatty alcohols have been found to be particularly effective as adjuvants in agricultural pesticide formulations. The monoglycosides are particularly preferred materials to utilize in agricultural pesticide formulations.

DETAILED DESCRIPTION OF THE INVENTION

Adjuvants for plant pesticide formulations have special requirements. They should have low mammalian toxicity, low irritation on dermal contact and be biodegradable. The organic glycosides useful in the present invention have properties which make them eminently suitable for use as adjuvants in plant pesticide formulations.

The wetting ability of an aqueous mixture containing an aliphatic polyglycoside or an aliphatic monoglycoside containing from about 7 to 18 carbon atoms in the aliphatic group can be improved by including in the aqueous mixture of the aliphatic glycoside and the material to be spread on the substrate a wetting improving amount of a fatty alcohol.

When the material is required to penetrate the substrate, the addition of the fatty alcohol can improve the rate of spreading of the aqueous mixture and the penetration of the substrate. The addition of the fatty alcohol to the aliphatic glycoside water mixture is particularly effective when the surface of the substrate comprises an oily or waxy surface layer. The aqueous mixture containing an aliphatic monoglycoside or an aliphatic polyglycoside with the added fatty alcohol more evenly wets the surface of the substrate and can aid in penetration of the waxy or oily surface of the substrate by the material spread on the surface.

The mixture of aliphatic glycoside and fatty alcohol of the present invention is particularly useful for use in hard surface cleaners and inclusion as an adjuvant in agricultural pesticide formulations. The composition of the aliphatic glycoside and fatty alcohol can be useful wherever increased wetting ability of an aqueous material is desired. The present invention can be useful in formulations that are applied to seeds, to the ground or directly to plants. Particularly, the composition of the present invention is effective as an adjuvant in agricultural pesticide formulations which are applied to the plant foliage. The composition of the present invention aids in a more rapid spread of the aqueous layer on the plant's leaf surface and more rapid absorption.

Plant pesticide compositions are generally formulated as dusts, wettable powders, granular compositions, liquid emulsions or suspensions or liquid concentrates. The composition of the present invention is particularly useful as an adjuvant in aqueous mixtures of agricultural pesticide formulations comprising wettable powders, suspensions, emulsions and soluble materials. The composition of the present invention is particularly useful in compositions containing the herbicide N-phosphomethyl glycine salts (glyphosate) which are water soluble.

In a concentrate, the adjuvant of the present invention aids in forming a more stable aqueous mixture; particularly, a more stable solution of a soluble material in a concentrated form. The monoglycosides containing from about 7 to about 12, and particularly 8 to about 10, carbon atoms in the alkyl group are particularly effective in stabilizing aqueous mixtures of water soluble materials.

The formulations containing the aliphatic monoglycosides or aliphatic polyglycosides alone or in combination with a fatty alcohol of this invention are advantageous in that they can be used in formulation of concentrates which contain a high concentration of the active pesticidal material, are thermally stable over a wide temperature range, are compatible with and dilutable in both hard and soft water and are also compatible and dilutable with nitrogenous fertilizer solutions.

The use of the adjuvant comprising an aliphatic monoglycoside or polyglycoside alone or in combination with a fatty alcohol are particularly useful in agricultural pesticidal formulations, since they are made from natural products and are readily biodegradable in the environment.

The adjuvant of the present invention is useful with water dispersible or water soluble materials. In general, the adjuvant of the present invention improves the wetting ability of the aqueous mixture, whether it be a suspension, dispersion or solution of a composition in an aqueous phase. The improved wetting ability of the mixture improves the coverage of a substrate with which the aqueous mixture comes in contact and in addition aids in penetration of the substrate by the material coated thereon when the substrate is an oily or waxy surface.

The aliphatic monoglycosides and aliphatic polyglycosides useful in the practice of the invention are well known materials and can be prepared by methods such as disclosed in U.S. Pat. No. 3,547,828, U.S. Pat. No. 3,598,865, U.S. Pat. No. 3,772,269 and U.S. Pat. No. 4,939,245, which are incorporated herein by reference. The aliphatic monoglycoside and aliphatic polyglycoside products generally contain small amounts of the fatty alcohol from which the glycosides are prepared. However, due to odor problems and for functional reasons, in regard to loss of detergency associated with fatty alcohol content in the aliphatic glycosides, the commercially available materials have free fatty alcohol contents below about 1% and generally below about 0.5% by weight of the aliphatic glycoside.

The fatty alcohol can be removed from the aliphatic glycoside product by the process disclosed in U.S. Pat. No. 4,393,203, which is incorporated herein by reference. U.S. Pat. No. 4,393,203 discloses the necessity for removing fatty alcohol from the alkyl glycoside composition.

Applicants have unexpectedly discovered that contrary to the practice in the art, inclusion of fatty alcohol in aliphatic glycoside compositions substantially improves the wetting ability of aqueous mixtures containing aliphatic glycosides which are to be applied to plant substrates.

Aliphatic glycosides useful in the practice of the present invention are compositions of the formula wherein R is an aliphatic hydrocarbon group which can be straight chain or branched, saturated or unsaturated having from about 7 to about 18 carbon atoms and preferably from about 7 to about 16 carbon atoms and most preferably from about 8 to about 12 carbon atoms. R' is H, $CH_3$ or $CH_3CH_2$; G is the residue of a reducing saccharide, preferably a glucose residue; y is an average number of from 0 to about 5; and x is an average degree of polymerization (DP) of from 1 to about 4 and preferably from 1 to about 2.5. The DP is an average of the number of glycose groups attached to an aliphatic group.

Particularly useful materials comprise the compositions where R is an alkyl or alkenyl group having from about 8 to about 12 carbon atoms, y is 0, G is a glucose residue and x is a number from 1 to about 1.15 and preferably 1 to about 1.1 and most preferably 1 to about 1.05 or less. Compositions within this range of a DP of from 1 to 1.15 are considered to be monoglycosides within the context of the present invention.

Generally, the low DP aliphatic glycoside compositions contain more than 60% of a monoglycoside and more preferably above about 80% monoglycoside and most preferably in the range of above about 90% by weight of the monoglycoside.

The aliphatic glycoside compositions available commercially contain less than about 1% by weight of fatty alcohol from which they are made and generally less than 0.5% by weight of fatty alcohol. As is understood in the art, more than about 0.5% of fatty alcohol in an aliphatic glycoside composition presents odor problems which make them unattractive for use in consumer products. However, the odor of a fatty alcohol is not a deterrent for use in agricultural pesticide application uses.

The compositions of the present invention which comprise the aliphatic glycoside and a fatty alcohol include the addition of at least 0.5% by weight of fatty alcohol to the mixture of aliphatic glycoside and fatty alcohol. This is in addition to the amount of fatty alcohol which is in the aliphatic glycoside composition as a result of the manufacturing process. The mixture of aliphatic glycoside and fatty alcohol useful in the practice of the present invention generally contains from above about 1% (including the fatty alcohol in the aliphatic glycoside as manufactured) to about 20% by weight of fatty alcohol, preferably from about 2 to about 15% by weight of fatty alcohol and most preferably from about 2 to about 10% by weight of fatty alcohol. The fatty alcohol added to the aliphatic glycoside compositions useful in the practice of the present invention need not be the same fatty alcohol used to manufacture the aliphatic glycoside.

When the aliphatic glycoside is an alkyl or alkenyl glycoside having a 7 to 10 carbon atom alkyl or alkenyl group, it is advantageous to add a fatty alcohol having from about 9 to about 12 carbon atoms to the aliphatic glycoside. Applicants have found the most effective wetting improvement obtained when the fatty alcohol added to the composition contains from 9 to 11 carbon atoms. Preferably the fatty alcohol is a fatty alcohol containing 10 carbon atoms or a mixture of fatty alcohols in which a fatty alcohol containing 10 carbon atoms is the major component.

The aliphatic glycoside useful in the practice of the present invention can contain the residues of a 5 or 6 membered reducing saccharides, such as glucose, mannose, galactose, arabinose, apiose, lyxose, galose, altrose, idose, ribose, xylose and talose. The aliphatic glycosides useful in the practice of the present invention can also be made from oligo and poly saccharides which under the acid conditions at which the compounds are made form the reducing saccharides residues. Oligo saccharides such as maltose, lactose, maltotriose, starch, starch hydrolyzates and high dextrose corn syrup can be utilized as the source of the glycose moiety in the aliphatic glycosides useful in the practice of the present invention. Preferably, the glycose moiety is a glucose residue, since glucose is readily available at a reasonable cost.

The aliphatic glycoside fatty alcohol adjuvant of the present invention is generally present in the aqueous mixture of the agricultural pesticide in relation to the pesticide which is to be coated on the substrate in a weight ratio of from about 5:1 to about 1:10 and preferably in a weight ratio of from about 3:1 to about 1:5 and most preferably in a weight ratio of from about 1.5:1 to 1:3.

The aliphatic glycoside fatty alcohol mixture can be mixed with the material to be spread on the substrate in a concentrated mixture which is later diluted to the application strength. The concentrated mixture can contain water, other surfactants and polar solvents which aid in dispersing the mixture in water. The concentrated mixture can contain hydrotropes, viscosity controlling materials and other adjuvants which can be present in aqueous mixtures to be coated on a substrate. Particularly, the compositions can contain the usual adjuvants which are present in agricultural pesticide formulations.

The aliphatic glycosides can be mixed with the material to be spread on the substrate as a dry mix, paste, emulsion, liquid mixtures and liquid mixtures containing water. In addition, the mixture of the aliphatic glycosides and the fatty alcohol can be added to an aqueous mixture of the material to be spread on the substrate and water at the dilution of use. That is, the mixture of aliphatic glycoside and fatty alcohol can be added directly to a diluted mixture of the material to be spread on the substrate with water.

Since it is known that aliphatic glycosides by themselves have pesticidal activity (U.S. Pat. No. 4,888,325, which is incorporated herein by reference) the invention encompasses a mixture comprising the aliphatic glycoside, fatty alcohol and water. The addition of the fatty alcohol to the aliphatic glycoside facilitates the spreading of the droplet on the surface on which it is deposited and can also facilitate and aid in penetration of the waxy layer of plant foliage to which a plant pesticide may be applied. The aliphatic glycoside-fatty alcohol adjuvants of the present invention are particularly useful for admixture with formulations of systemic agricultural pesticides which are generally applied to the leaf surfaces. The mixture of the aliphatic glycoside and fatty alcohol aids in penetration of the leaf and permits the agricultural pesticide to enter the plant through the leaf surface more rapidly. The mixture is particularly effective with salts of N-phosphonomethyl glycine which are known to enter the plant's circulation system and bind to certain critical components at a cellular level. The mixture can also be useful with systemic fungicides such as Fosytel-Al.

The increase in wetting rate and spreading on an oily or waxy surface is important for agricultural pesticide materials which must be spread on the surface of a leaf. Generally, an aqueous mixture containing the agricultural pesticide is sprayed onto the leaf surface. Under normal circumstances, the mixture is sprayed onto a plant surface under hot dry conditions. The aqueous droplets which are deposited on the leaf's surface have a limited time to spread over the surface, since the water droplets rapidly dry under hot, substantially dry conditions. The larger the area which an individual drop can cover before drying improves the effectiveness of the pesticide. If the pesticide is to be absorbed through the leaf's surface, the addition of the aliphatic glycoside containing the fatty alcohol improves the rate of penetration and in addition the increased area covered by the water droplet before it dries provides for a larger area for penetration and absorption. If the agricultural pesticide is not to be absorbed through the leaf's surface but is to remain on the surface to contact insects or combat fungus infestations, the increase in rate of spreading of the liquid droplet provides for coverage of a larger area by a single drop before drying occurs. The larger area provides for a greater contact with the fungus or a larger area for an insect to contact the insecticidal material.

The increased wetting effect of the addition of the aliphatic glycoside and the fatty alcohol to an aqueous mixture was tested according to a Draves Wetting Time Test, which is a test for the wetting power of a surfactant for cotton.

The wetting power was also tested by a test devised to simulate the surface of a leaf. In the test, a drop of the aqueous mixture containing the aliphatic glycoside and fatty alcohol is deposited on a microscope slide covered with a uniform waxy layer. The change in the contact angle between the water droplet and the waxy substrate is measured on a periodic basis. The decrease in time for the contact angle to reach zero is an indication of the improvement in wetting and penetration properties of the mixture of aliphatic glycoside and fatty alcohol in water.

The Draves Wetting Time does not correlate well with the measurement of the contact angle in determining the increased wetting power of the mixture. Mixtures which have a low Draves Wetting Time do not show a dramatic decrease in wetting time by addition of the mixture of fatty alcohol and alkyl glycoside. However, measurement of the contact angle vs. time shows a substantial increase in wetting ability even in alkyl glycoside-fatty alcohol mixtures which do not show a dramatic reduction in Draves Wetting Time.

The following materials were used in carrying out the experiments in the examples.

| | | |
|---|---|---|
| $C_8$–$C_{10}$ glucoside DP 1.7 | Ratio $C_8$/$C_{10}$ | 45/55 |
| $C_9$–$C_{10}$–$C_{11}$ alkyl glucoside DP 1.6 | Ratio $C_9$/$C_{10}$/$C_{11}$ | 20/40/40 |
| $C_9$–$C_{10}$–$C_{11}$ alkyl glucoside DP 1.4 | Ratio $C_9$/$C_{10}$/$C_{11}$ | 20/40/40 |
| $C_{12}$–$C_{14}$–$C_{16}$ alkyl glucoside DP 1.6 | Ratio $C_{12}$/$C_{14}$/$C_{16}$ | 68/26/6 |
| $C_8$–$C_{10}$–$C_{12}$–$C_{14}$–$C_{16}$ alkyl glucoside DP 1.6 | Ratio $C_8$/$C_{10}$/$C_{12}$/$C_{14}$/$C_{16}$ | 30/37/22/9/2 |
| $C_8$–$C_{10}$ alkyl alcohol | Ratio $C_8$/$C_{10}$ | 45/55 |
| $C_9$–$C_{10}$–$C_{11}$ alkyl alcohol | Ratio $C_9$/$C_{10}$/$C_{11}$ | 20/40/40 |
| $C_{12}$–$C_{14}$–$C_{16}$ alkyl alcohol | Ratio $C_{12}$/$C_{14}$/$C_{16}$ | 68/26/6 |
| $C_8$ alkyl alcohol | | |
| $C_{10}$ alkyl alcohol | | |
| $C_{12}$ alkyl alcohol | | |

Example 1

An alkyl polyglucoside having alkyl groups containing 8 and 10 carbon atoms and a DP of 1.7 was tested to determine the Draves Wetting Time. The alkyl glycoside had a free fatty alcohol content of less than 0.5% by weight of the mixture. A 0.1% aqueous solution of the $C_8$-$C_{10}$ alkyl polyglucoside with a DP of 1.7 was measured and varying proportions of a $C_8$-$C_{10}$ alcohol was added to the mixture. The addition of the fatty alcohol substantially increased the wetting rate (decreased the wetting time) of the mixture of the alkyl glucoside and water. The 0.1% concentration was the concentration of the mixture of the alkyl polyglucoside and the free fatty alcohol. The Draves wetting times of the aqueous solutions were as follows.

TABLE 1

| % $C_8$–$C_{10}$ Alkyl Glucoside | % Free Fatty Alcohol | Draves Wetting Time |
|---|---|---|
| 100 | 0 | over 15 min. |
| 98.6 | 1.4 | between 7 & 10 min. |
| 97.2 | 2.8 | 330 sec. |
| 94.5 | 5.5 | 80 sec. |
| 89.0 | 11.0 | 49 sec. |

The addition of the fatty alcohol to the alkyl glucoside reduced the foam produced by the mixture. This can be useful in applications where large amounts of foam are not required or are a detriment to the application. The alcohol added in this example was in addition to the small amount of fatty alcohol which was in the alkyl glucoside composition as produced.

Example 2

A sample of a $C_9$-$C_{10}$-$C_{11}$ alkyl polyglucoside with a DP of 1.7 and a free fatty alcohol content of less than 0.7% by weight was dried in a vacuum oven for 64 hours at 90° C. and full water vacuum. The Draves Wetting Time of a 0.1% solution of the alkyl polyglucoside and an alkyl polyglucoside containing added free fatty alcohol having $C_9$-$C_{10}$-$C_{11}$ carbon atoms was determined.

TABLE 2

| % Free Alcohol Added | Draves Wetting Time | Ross Miles Foam Height | |
|---|---|---|---|
| | | 0 min | 5 min |
| 0 | 31.6 sec. | 145 | 145 |
| 0.25 | 29.2 sec. | 140 | 140 |
| 0.5 | 26.2 sec. | 145 | 145 |
| 1.0 | 27.2 sec. | 140 | 140 |
| 1.25 | 27.0 sec. | 140 | 140 |
| 2.5 | 21.4 sec. | 145 | 145 |
| 5.0 | 16.6 sec. | 145 | 145 |

The data in the table clearly shows that the Draves Wetting Time of an aqueous solution of an alkyl polyglucoside and water can be substantially reduced by the inclusion of free fatty alcohol in the mixture. Five percent of free fatty alcohol reduced the Draves wetting time by about 50%. In the solutions (0.1% by weight solids) the addition of the fatty alcohol did not substantially affect the foam generated by the mixture.

Example 3

The Draves Wetting Times of a 0.1% solution of a mixture of a $C_8$-$C_{10}$ (45/55) alkyl glucoside with a DP of 1.7 and a $C_8$, a $C_{10}$ and a $C_{12}$ fatty alcohol at levels of 1%, 2.5% and 5% by weight of the mixture were determined. The alkyl polyglucoside had a fatty alcohol content of less than 0.5% by weight. The additions in the table are the percent of free fatty alcohol which were added to the alkyl polyglucoside based on the weight of the alkyl polyglucoside and the added free fatty alcohol. The Draves Wetting Time of the alkyl polyglucoside without any additional fatty alcohol was 119 seconds.

TABLE 3

| | Draves Wetting Time | | |
|---|---|---|---|
| Alcohol | 1% Fatty Alcohol | 2.5% Fatty Alcohol | 5% Fatty Alcohol |
| $C_8$ | 66.3 sec. | 43 sec. | 45.3 sec. |
| $C_{10}$ | 47.3 sec. | 39.7 sec. | 28 sec. |
| $C_{12}$ | 65.6 sec. | 49.7 sec. | 47.7 sec. |

The $C_{10}$ fatty alcohol addition had the greatest effect on the Drayes Wetting Time of the $C_8$-$C_{10}$ alkyl polyglucoside with a DP of 1.7. The reduction in the Draves Wetting Time was substantial even at a 1% addition of the fatty alcohol. The $C_{10}$ fatty alcohol appeared to have the greatest effect in reduction of the Draves wetting time. The experiment was limited to the addition of 5% fatty alcohol. However, the data in the table indicates that the Draves wetting time would have been further reduced if more than 5% of the $C_{10}$ fatty alcohol were added to the alkyl polyglucoside.

Example 4

A comparison of the spreading rate of an alkyl polyglucoside with an alkyl group $C_9$-$C_{10}$-$C_{11}$ (20/40/40) with a DP of 1.4 and a fatty alcohol content of less than 0.5% by weight was made with the same alkyl polyglucoside containing added fatty alcohol by the contact angle method. One percent by weight solution of the alkyl polyglucoside, and a one percent by weight solution of a mixture of the alkyl polyglucoside containing 5.0% of a $C_{12}$-$C_{14}$-$C_{16}$ fatty alcohol were prepared.

A substrate which approximates the waxy surface of plant foliage was prepared by placing an 8 cm×3 cm strip of PARAFILM ® M (a paraffin wax material) on a microscope slide. The PARAFILM® M was arranged to be smooth and flat. The slide covered with the waxy film was then placed on the stage of a goniometer. Ten microliters of a 1% solution of surfactant or mixture of surfactant and fatty alcohol in water was placed on the waxy surface of the substrate and a stopwatch started. The contact angle of the droplet was recorded every 2 minutes. The results of the test are shown in Table 4.

TABLE 4

| TIME Minutes | CONTACT ANGLE | |
|---|---|---|
| | Alkyl Polyglucoside $C_9$—$C_{10}$—$C_{11}$ | Alkyl Polyglucoside + 5% $C_{12}$—$C_{14}$—$C_{16}$ Fatty Alcohol |
| 0 | 42 | 36 |
| 2 | 35 | 29 |
| 4 | 31 | 27 |
| 6 | 28 | 24 |
| 8 | 25 | 22 |
| 10 | 24 | 20 |
| 12 | 21 | 18 |
| 14 | 20 | 16 |
| 16 | 18 | 14 |
| 18 | 16 | 12 |
| 20 | 14 | 10 |
| 22 | 12 | 8 |
| 24 | 9 | 5 |
| 26 | 7 | 4 |
| 28 | 5 | 2 |
| 30 | 3 | 0 |
| 32 | 2 | |
| 34 | 0 | |

The results of the test clearly show that the addition of the fatty alcohol to the aqueous solution of the alkyl glucoside increases the rate of wetting and the penetration of the solution into the paraffin substrate.

The test was developed to provide a rapid screening method for determining the rate of wetting and penetration of surfactant solutions into waxy leaf substrates. The test is a more accurate method for determining the rate of wetting a waxy surface than the Draves Wetting Time. The Draves Wetting Time measures the rate of wetting of a cotton substrate and is more closely related to washing and dyeing of textile materials A substantial increase in the rate at which a waxy substrate is wetted is not always reflected in a decrease in the Draves Wetting Time.

A series of experiments were carried out in which varying concentrations of a fatty alcohol (FOH) were added to various alkyl glucosides and the contact angle with a waxy substrate was measured according to the method of Example 4.

Example 5

A 1% solution of an alkyl glucoside prepared from a mixture of a $C_8$–$C_{10}$ alcohol with a degree of polymerization (DP) of 1.7 and a 1% solution of the $C_8$–$C_{10}$ alkyl polyglucoside and mixtures with varying proportions of fatty alcohols were prepared. The contact angle of the solutions with a waxy substrate was measured according to the method of Example 4. The 1% solution was based on the total weight of the mixture of alkyl glucoside and fatty alcohol added to the alkyl glucoside.

Figure 1:
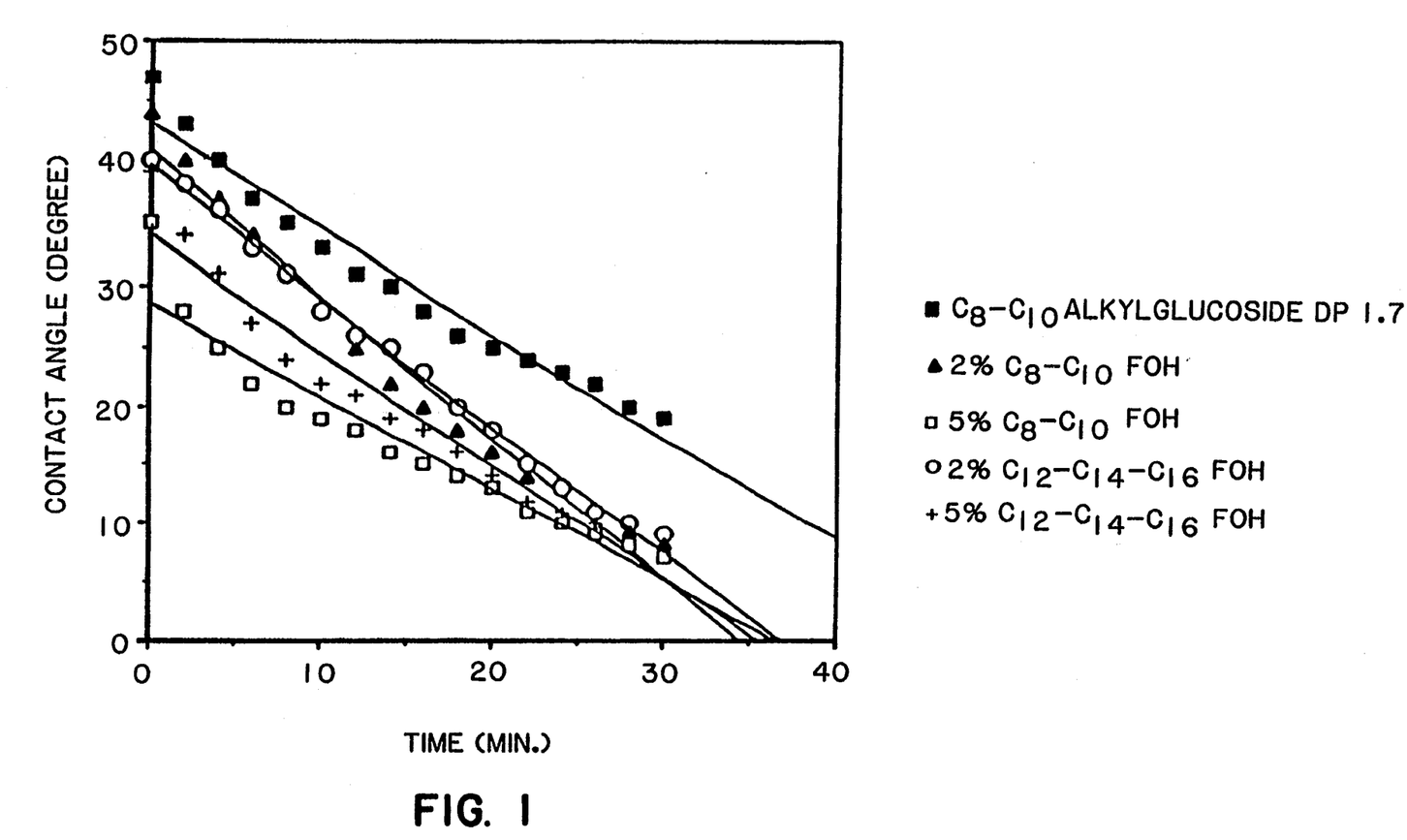
FIG. 1 is a graph of Contact Angle vs. Time for a 1.0% by weight aqueous solution of a $C_8$–$C_{10}$ glucoside with a DP of 1.7 and a mixture of the $C_8$–$C_{10}$ aliphatic glucoside with fatty alcohol.

The results of the experiments are shown in table 5 and the plot of the data is shown in FIG. 1. It can be seen from FIG. 1 that the addition of a small amount of fatty alcohol to the alkyl glucoside substantially increases the rate of wetting (decrease in contact angle) of the waxy substrate by the aqueous mixture.

TABLE 5

| TIME Minutes | CONTACT ANGLE | | | | |
|---|---|---|---|---|---|
| | $C_8$—$C_{10}$ Alkyl-glucoside | $C_8$—$C_{10}$ Alkyl-glucoside + 2% $C_8$—$C_{10}$ FOH | $C_8$—$C_{10}$ Alkyl-glucoside + 5% $C_8$—$C_{10}$ FOH | $C_8$—$C_{10}$ Alkyl-glucoside + 2% $C_{12}$—$C_{14}$—$C_{16}$ FOH | $C_8$—$C_{10}$ Alkyl-glucoside + 5% $C_{12}$—$C_{14}$—$C_{16}$ FOH |
| 0 | 47 | 44 | 35 | 40 | 39 |
| 2 | 43 | 40 | 28 | 38 | 34 |
| 4 | 40 | 37 | 25 | 36 | 31 |
| 6 | 37 | 34 | 22 | 33 | 27 |
| 8 | 35 | 31 | 20 | 31 | 24 |
| 10 | 33 | 28 | 19 | 28 | 22 |
| 12 | 31 | 25 | 18 | 26 | 21 |
| 14 | 30 | 22 | 16 | 25 | 19 |
| 16 | 28 | 20 | 15 | 23 | 18 |
| 18 | 26 | 18 | 14 | 20 | 16 |
| 20 | 25 | 16 | 13 | 18 | 14 |
| 22 | 24 | 14 | 11 | 15 | 12 |
| 24 | 23 | 13 | 10 | 13 | 11 |
| 26 | 22 | 11 | 9 | 11 | 10 |
| 28 | 20 | 9 | 8 | 10 | 9 |
| 30 | 19 | 8 | 7 | 9 | 8 |

Example 6

A 1% solution of an alkyl glucoside having a DP of 1.6 prepared from a mixture of $C_9$-$C_{10}$-$C_{11}$ alcohol was prepared. Various proportions of a $C_8$-$C_{10}$ fatty alcohol or a $C_{12}$-$C_{14}$-$C_{16}$ fatty alcohol were added to the alkyl glucoside and the contact angle determined according to the method of Example 4.

Figure 2:
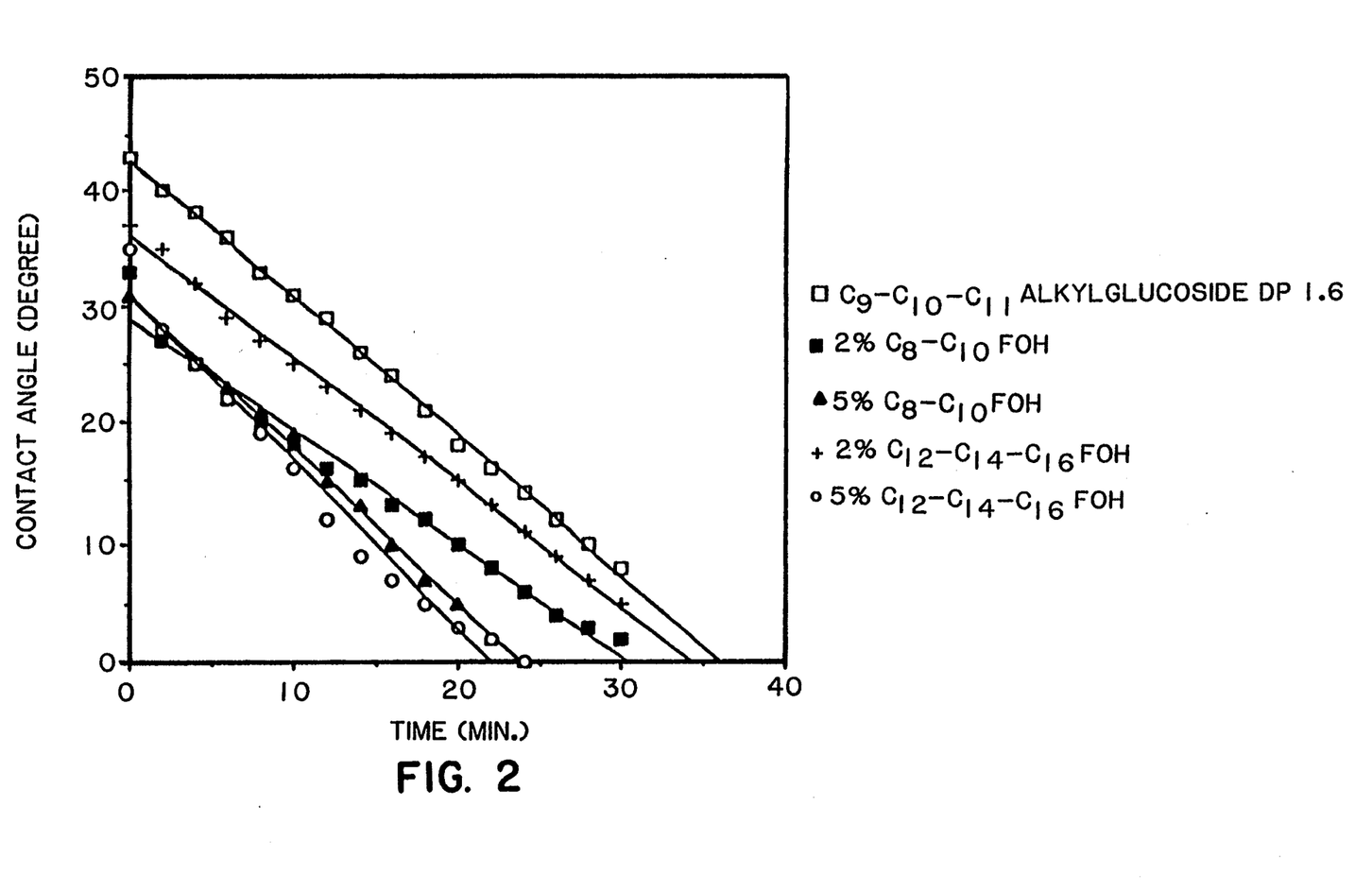
FIG. 2 is a graph of Contact Angle vs. Time for a 1.0% by weight aqueous solution of a $C_9$–$C_{10}$–$C_{11}$ aliphatic glucoside with a DP of 1.6 and mixtures of the $C_9$–$C_{10}$–$C_{11}$ aliphatic glucoside and varying percentages of fatty alcohol.

The results of the tests are shown in Table 6 and a plot of the data is shown in FIG. 2. The data clearly shows that the addition of a fatty alcohol to the alkyl glucoside has a substantial effect on the contact angle between the water droplet and the waxy substrate. The data clearly shows that the wetting ability and penetration of the solution containing the alkyl glucoside and the fatty alcohol is substantially increased or the wetting ability of a solution of the alkyl glucoside alone.

TABLE 6

| | | CONTACT ANGLE | | | |
|---|---|---|---|---|---|
| TIME Minutes | $C_9$–$C_{10}$–$C_{11}$ Alkyl-glucoside | $C_9$–$C_{10}$–$C_{11}$ Alkyl-glucoside + 2% $C_8$–$C_{10}$ FOH | $C_9$–$C_{10}$–$C_{11}$ Alkyl-glucoside + 5% $C_8$–$C_{10}$ FOH | $C_9$–$C_{10}$–$C_{11}$ Alkyl-glucoside + 2% $C_{12}$–$C_{14}$–$C_{16}$ FOH | $C_{98}$–$C_{10}$–$C_{11}$ Alkyl-glucoside + 5% $C_{12}$–$C_{14}$–$C_{16}$ FOH |
| 0 | 43 | 33 | 31 | 37 | 35 |
| 2 | 40 | 27 | 28 | 35 | 28 |
| 4 | 38 | 25 | 25 | 32 | 25 |
| 6 | 36 | 22 | 23 | 29 | 22 |
| 8 | 33 | 20 | 21 | 27 | 19 |
| 10 | 31 | 18 | 19 | 25 | 16 |
| 12 | 29 | 16 | 15 | 23 | 12 |
| 14 | 26 | 15 | 13 | 21 | 9 |
| 16 | 24 | 13 | 10 | 19 | 7 |
| 18 | 21 | 12 | 7 | 17 | 5 |
| 20 | 18 | 10 | 5 | 15 | 3 |
| 22 | 16 | 8 | 2 | 13 | 2 |
| 24 | 14 | 6 | 0 | 11 | 0 |
| 26 | 12 | 4 | | 9 | |
| 28 | 10 | 3 | | 7 | |
| 30 | 8 | 2 | | 5 | |

Example 7

Figure 3:
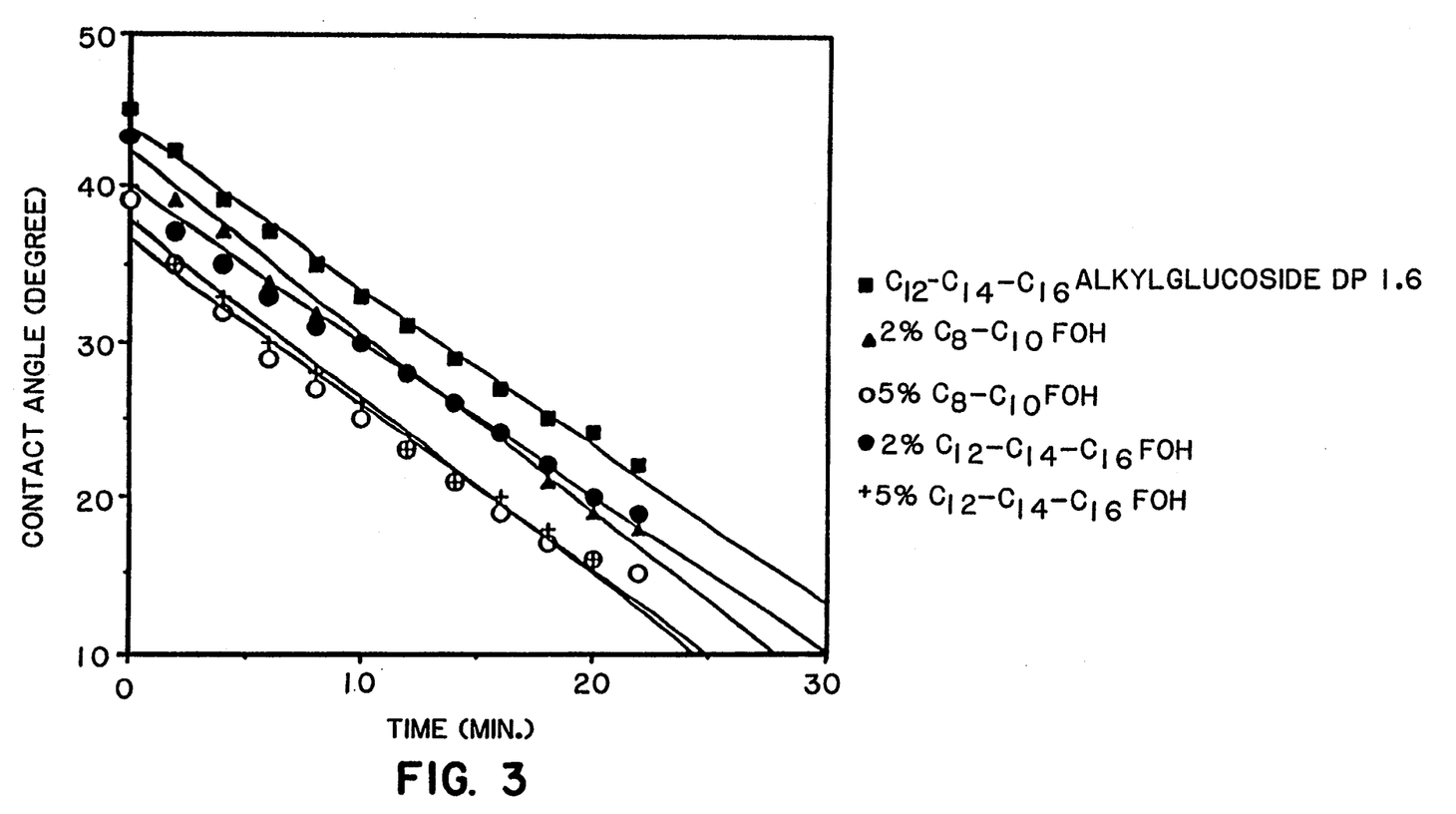
FIG. 3 is a graph of Contact Angle vs. Time for a 1.0% by weight aqueous solution of a $C_{12}$–$C_{14}$–$C_{16}$ aliphatic glucoside with a DP of 1.6 and mixtures of the $C_{12}$–$C_{14}$–$C_{16}$ aliphatic glucosides with fatty alcohol.

The wetting ability for a waxy substrate of a $C_{12}$-$C_{14}$$C_{16}$ alkyl glucoside with a DP of 1.6 was determined by preparing a 1% solution of the alkyl glucoside in distilled water and measuring the contact angle between a drop of the water and a waxy substrate according to the procedure of Example 4. Samples containing 1% of a mixture of the $C_{12}$-$C_{14}$-$C_{16}$ alkyl glucoside and 2% or 5% by weight of a fatty alcohol were prepared and tested. The results of the experiment are shown in Table 7 and a plot of the data is shown in FIG. 3. The data indicates that both the $C_8$-$C_{10}$ FOH and the $C_{12}$-$C_{14}$-$C_{16}$ FOH were effective at 2% and the 5% by weight of the mixture of alkyl glucoside and alcohol in increasing the wetting and penetration ability of water droplets containing the mixture.

substrate were measured according to the method of Example 4. One percent solutions of a mixture of 2% and 5% by weight of a fatty alcohol and the alkyl glucoside were prepared and the contact angle between water droplets containing 1% of the surfactant mixture and a paraffin wax substrate were measured.

Figure 4:
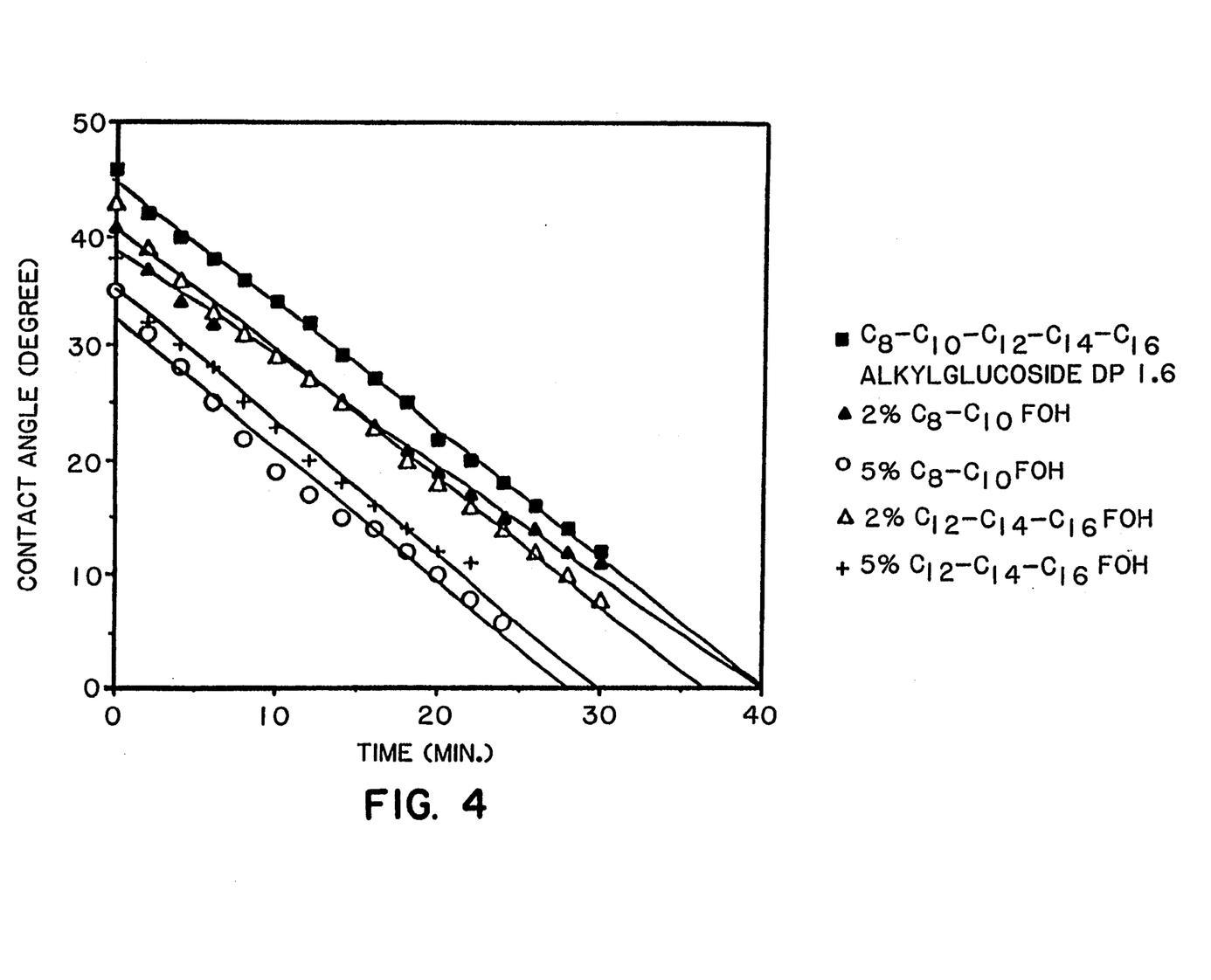
FIG. 4 is a graph of Contact Angle vs. Time for a 1.0% by weight aqueous solution of a $C_8$–$C_{10}$–$C_{12}$–$C_{14}$–$C_{16}$ aliphatic glucoside DP 1.6 and mixtures of the $C_8$–$C_{10}$–$C_{12}$–$C_{14}$–$C_{16}$ aliphatic glucoside with fatty alcohol.

The data from the experiment is set forth in Table 8. A plot of the data in Table 8 appears as FIG. 4. The data shows that the contact angle between the waxy substrate and the water droplet is reduced more rapidly by a mixture of alkyl glucoside and fatty alcohol than by the solution of the alkyl glucoside without the addition of the fatty alcohol. The addition of 5% of the fatty alcohol to the alkyl glucoside was more effective in decreasing the contact angle than the 2% addition of fatty alcohol.

The reduction in the contact angle is an indication of

TABLE 7

| | | CONTACT ANGLE | | | |
|---|---|---|---|---|---|
| TIME Minutes | $C_{12}$–$C_{14}$–$C_{16}$ Alkyl-glucoside | $C_{12}$–$C_{14}$–$C_{16}$ Alkyl-glucoside + 2% $C_8$–$C_{10}$ FOH | $C_{12}$–$C_{14}$–$C_{16}$ Alkyl-glucoside + 5% $C_8$–$C_{10}$ FOH | $C_{12}$–$C_{14}$–$C_{16}$ Alkyl-glucoside + 2% $C_{12}$–$C_{14}$–$C_{16}$ FOH | $C_{12}$–$C_{14}$–$C_{16}$ Alkyl-glucoside + 5% $C_{12}$–$C_{14}$–$C_{16}$ FOH |
| 0 | 45 | 45 | 39 | 43 | 40 |
| 2 | 42 | 39 | 35 | 37 | 35 |
| 4 | 39 | 37 | 32 | 35 | 33 |
| 6 | 37 | 34 | 29 | 33 | 30 |
| 8 | 35 | 32 | 27 | 31 | 28 |
| 10 | 33 | 30 | 25 | 30 | 26 |
| 12 | 31 | 28 | 23 | 28 | 23 |
| 14 | 29 | 26 | 21 | 26 | 21 |
| 16 | 27 | 24 | 19 | 24 | 20 |
| 18 | 25 | 21 | 17 | 22 | 18 |
| 20 | 24 | 19 | 16 | 20 | 16 |
| 22 | 22 | 18 | 15 | 19 | |
| 24 | | | | | |
| 26 | | | | | |
| 28 | | | | | |
| 30 | | | | | |

Example 8

A 1% mixture of a $C_8$-$C_{10}$-$C_{12}$-$C_{14}$-$C_{16}$ (30/37/22/9/2) alkyl glucoside with a DP of 1.6 was prepared as a 1% solution and the contact angle between a water droplet of the solution and a paraffin wax a more rapid wetting and spreading of the water droplet over the surface of the waxy substrate. The more rapidly the water droplet spreads (more rapid reduction in the contact angle) permits the droplet to cover a larger area of the waxy surface in a shorter time period. On a plant, the more rapid spreading of the water droplet permits the water droplet containing the agricultural pesticide or agricultural fertilizer to cover a larger area of a leaf and therefore provide a larger area for absorption or contact with fungus or an insect, before the water droplet dries and becomes substantially immobile.

5% by weight of a $C_{12}$-$C_{14}$-$C_{16}$ FOH were prepared. A 1% solution in water of the particular glucoside or the mixture of the glucoside and fatty alcohol was prepared and the contact angle measured according to the method of Example 4.

Figure 5:
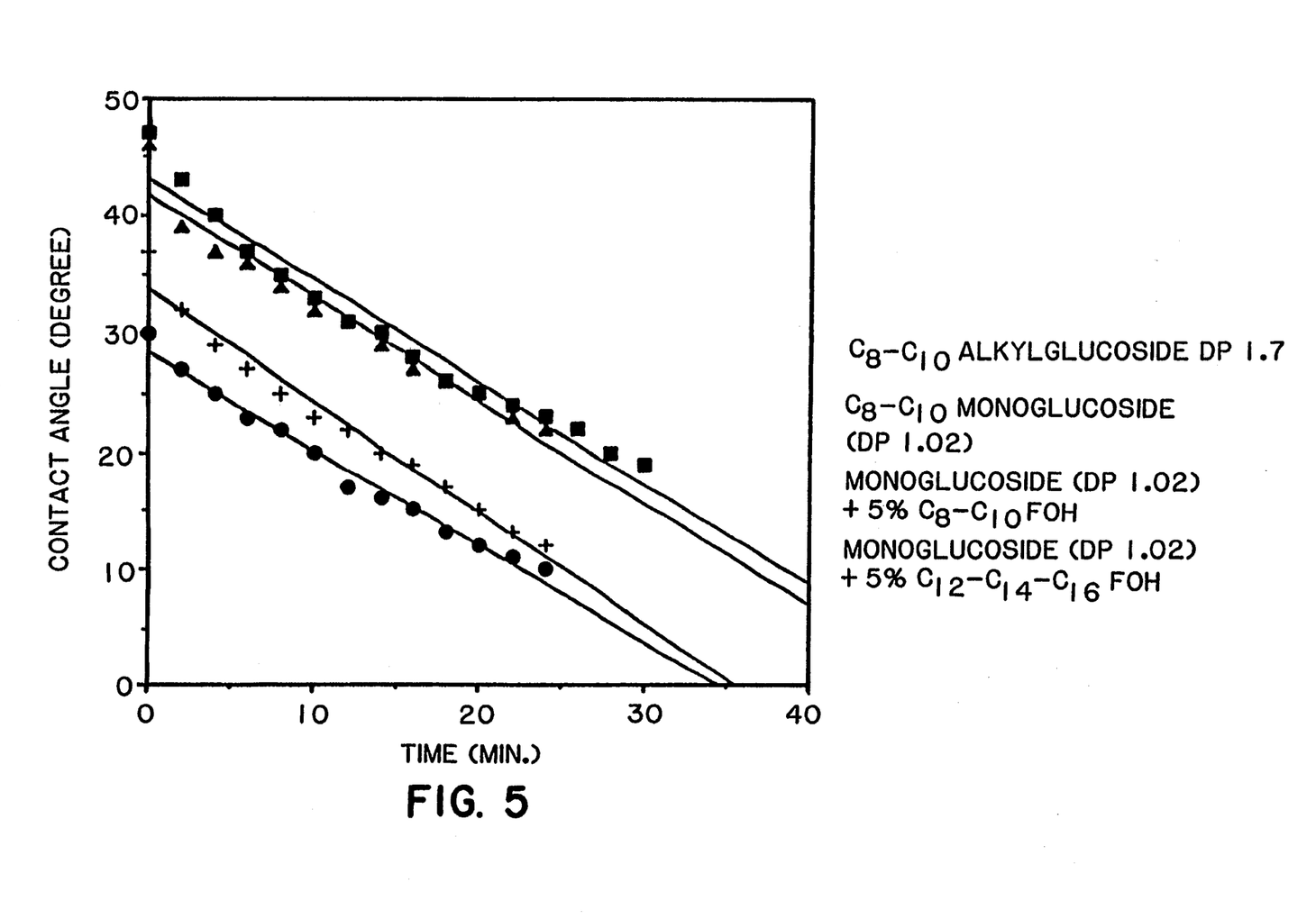
FIG. 5 is a graph of Contact Angle vs Time for a 1.0% by weight solution of a $C_8$–$C_{10}$ aliphatic glucoside DP 1.7, a $C_8$–$C_{10}$ aliphatic glucoside DP 1.02 and mixture of the $C_8$–$C_{10}$ aliphatic glucoside DP 1.02 with fatty alcohol.

The data from the experiment is shown in Table 9 and a plot of the data of Table 9 is shown in FIG. 5.

TABLE 8

| | CONTACT ANGLE | | | | |
|---|---|---|---|---|---|
| TIME Minutes | $C_8$—$C_{10}$—$C_{12}$—$C_{14}$—$C_{16}$ Alkyl-glucoside | $C_8$—$C_{10}$ $C_{12}$—$C_{14}$—$C_{16}$ Alkyl-glucoside + 2% $C_8$-$C_{10}$ FOH | $C_8$—$C_{10}$ $C_{12}$—$C_{14}$—$C_{16}$ Alkyl-glucoside + 5% $C_8$-$C_{10}$ FOH | $C_8$—$C_{10}$— $C_{12}$—$C_{14}$—$C_{16}$ Alkyl-glucoside + 2% $C_{12}$—$C_{14}$—$C_{16}$ FOH | $C_8$—$C_{10}$— $C_{12}$—$C_{14}$—$C_{16}$ Alkyl-glucoside + 5% $C_{12}$—$C_{14}$—$C_{16}$ FOH |
| 0 | 46 | 41 | 35 | 43 | 38 |
| 2 | 42 | 37 | 31 | 39 | 32 |
| 4 | 40 | 34 | 28 | 36 | 30 |
| 6 | 38 | 32 | 25 | 33 | 28 |
| 8 | 36 | 31 | 22 | 31 | 25 |
| 10 | 34 | 29 | 19 | 29 | 23 |
| 12 | 32 | 27 | 17 | 27 | 20 |
| 14 | 29 | 25 | 15 | 25 | 18 |
| 16 | 27 | 23 | 14 | 23 | 16 |
| 18 | 25 | 21 | 12 | 20 | 14 |
| 20 | 22 | 19 | 10 | 18 | 12 |
| 22 | 20 | 17 | 8 | 16 | 11 |
| 24 | 18 | 15 | 6 | 14 | |
| 26 | 16 | 14 | | 12 | |
| 28 | 14 | 12 | | 10 | |
| 30 | 12 | 11 | | 8 | |

TABLE 9

| | CONTACT ANGLE | | | |
|---|---|---|---|---|
| TIME Minutes | $C_8$—$C_{10}$ Alkyl-glucoside DP 1.7 | $C_8$—$C_{10}$ Monoglucoside | $C_8$—$C_{10}$ Monoglucoside + 5% $C_8$-$C_{10}$ Alcohol | $C_8$—$C_{10}$ Monoglucoside + 5% $C_{12}$—$C_{14}$—$C_{16}$ Alcohol |
| 0 | 47 | 46 | 30 | 37 |
| 2 | 43 | 39 | 27 | 32 |
| 4 | 40 | 37 | 25 | 29 |
| 6 | 37 | 36 | 23 | 27 |
| 8 | 35 | 34 | 22 | 25 |
| 10 | 33 | 32 | 20 | 23 |
| 12 | 31 | 31 | 17 | 22 |
| 14 | 30 | 29 | 16 | 20 |
| 16 | 28 | 27 | 15 | 19 |
| 18 | 26 | 26 | 13 | 17 |
| 20 | 25 | 25 | 12 | 15 |
| 22 | 24 | 23 | 11 | 13 |
| 24 | 23 | 22 | 10 | 12 |
| 26 | 22 | | | |
| 28 | 20 | | | |
| 30 | 19 | | | |

Example 9

Example 9 reports the results of an experiment in which the contact angle between a droplet of water and a paraffin wax substrate was determined for a $C_8$-$C_{10}$ alkyl glucoside with a DP of 1.7 and a $C_8$-$C_{10}$ alkyl glucoside with a DP of 1.02 (monoglucoside). The $C_8$-$C_{10}$ alkyl glucoside with DP 1.02 is substantially a glucoside in which one glucose moiety is associated with one $C_8$-$C_{10}$ alkyl moiety. Mixtures of the $C_8$-$C_{10}$ monoglucoside with 5% of a $C_8$-$C_{10}$ fatty alcohol (FOH) and a mixture of the $C_8$-$C_{10}$ monoglucoside with Example 10

The contact angles of a 0.8% solution of glyphosate isopropylamine salt, a 0.8% glyphosate isopropylamine salt solution containing 1% of a $C_8$-$C_{10}$ alkyl glucoside with a DP of 1.7, and a 0.8% solution of glyphosate isopropylamine salt containing 1% of a mixture of a $C_8$-$C_{10}$ alkyl glucoside with a DP of 1.7 and 5% of a $C_8$-$C_{10}$ fatty alcohol was also measured according to the method of Example 4.

Figure 6:
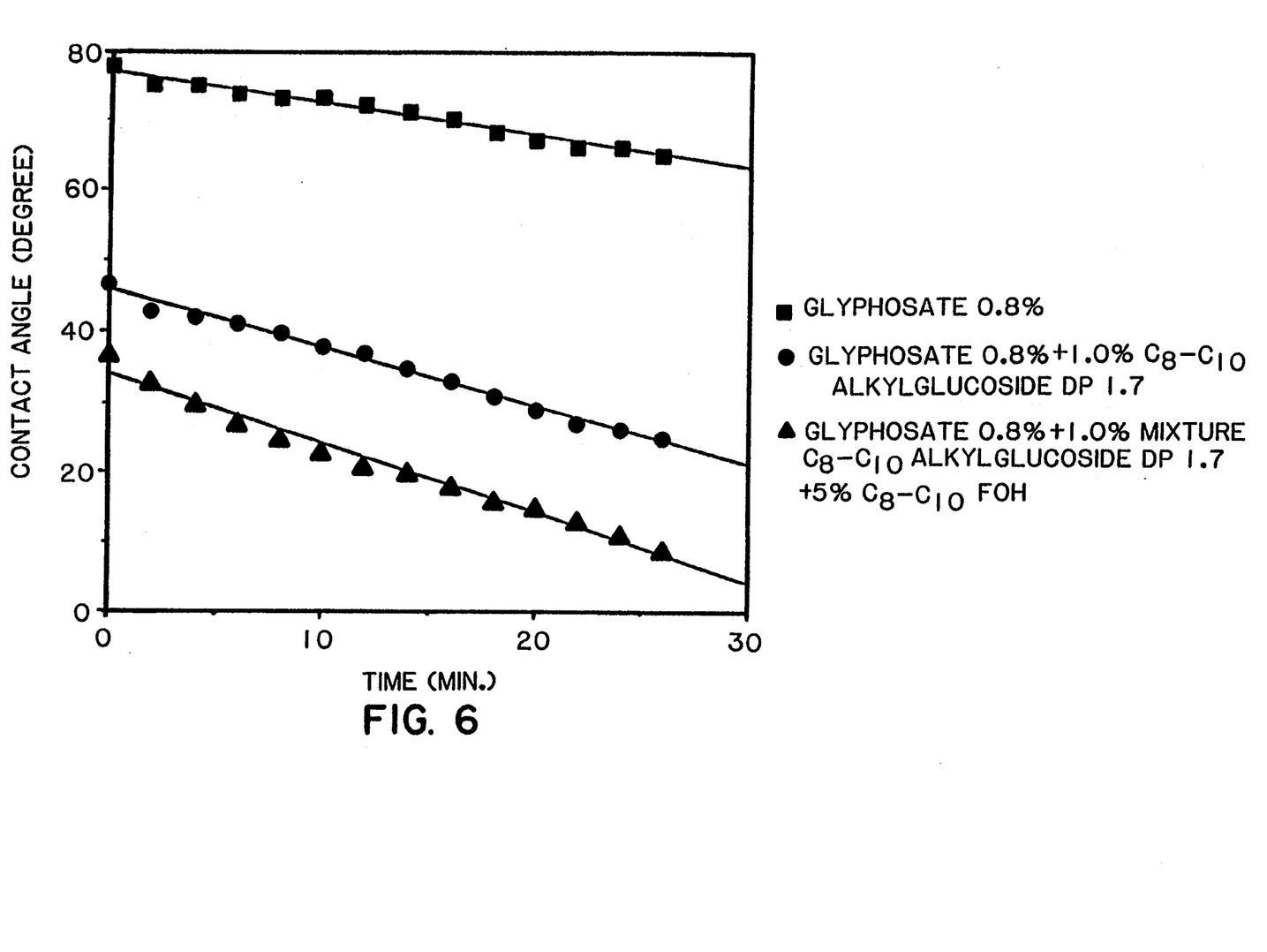
FIG. 6 is a graph of Contact Angle vs Time for a 0.8% by weight solution of glyphosate isopropylamine salt, and a 0.8% by weight glyphosate isopropylamine salt solution containing 1.0% by weight of a $C_8$–$C_{10}$ aliphatic glucoside DP 1.7 and a mixture of the $C_8$–$C_{10}$ aliphatic glucoside DP 1.7 with a $C_8$–$C_{10}$ fatty alcohol.

The data from the experiments are shown in Table 10. FIG. 6 is a plot of the data of Table 10.

TABLE 10

| | CONTACT ANGLE | | |
|---|---|---|---|
| TIME Minutes | 0.8% Glyphosate | 0.8% Glyphosate + 1.0% $C_8$—$C_{10}$ Alkylglucoside DP 1.7 | 0.8% Glyphosate 1.0% Mixture $C_8$—$C_{10}$ Alkylglucoside DP 1.7 + 5% $C_8$—$C_{10}$ FOH |
| 0  | 78 | 47 | 37 |
| 2  | 75 | 43 | 33 |
| 4  | 75 | 43 | 30 |
| 6  | 74 | 41 | 27 |
| 8  | 73 | 40 | 25 |
| 10 | 73 | 38 | 23 |
| 12 | 72 | 37 | 21 |
| 14 | 71 | 35 | 20 |
| 16 | 70 | 33 | 18 |
| 18 | 68 | 31 | 16 |
| 20 | 67 | 29 | 15 |
| 22 | 66 | 27 | 13 |
| 24 | 66 | 26 | 11 |
| 26 | 65 | 25 | 9 |
| 28 | | | |
| 30 | | | |

The data from the experiment clearly shows that the addition of a $C_8$-$C_{10}$ alkyl glucoside to the glyphosate isopropylamine salt solution substantially increases the wetting power of the solution. The wetting power is further increased when 1% of a mixture of a $C_8$-$C_{10}$ alkyl glucoside with a DP of 1.7 containing 5% by weight of a $C_8C_{10}$ fatty alcohol is added to the glyphosate solution. The glyphosate is in solution in the water and the alkyl glucoside and fatty alcohol mixture is particularly effective in increasing the wetting ability of the solution.

An analysis of the data presented in the examples clearly illustrates that the inclusion of a fatty alcohol in an alkyl glycoside aqueous solution substantially increases the wetting power of an aqueous solution containing the mixture. The wetting ability of a water droplet containing an agricultural pesticide is also increased by the inclusion of a mixture of an alkyl glycoside and a fatty alcohol in the pesticide containing mixture.

The mixture of an alkyl glycoside and fatty alcohol is a useful adjuvant to agricultural pesticide formulations which are applied to plant surfaces in an aqueous solution, since the ability of the solution to wet the plant surface is substantially improved. The alkyl glycosides and the fatty alcohol mixtures utilized in the practice of the present invention are formed from natural products and are readily biodegradable. The biodegradability of the composition of the present invention enhances its usefulness since it does not build up in the soil, has a pesticidal activity and its mammalian toxicity is extremely low.

The present invention is particularly useful for improving the spreading of aqueous mixtures containing agricultural materials on solid substrates. The improved wetting properties provided by the addition of an alkyl glycoside containing a portion of fatty alcohol substantially improves the ability of the aqueous mixture to contact the substrate to which it is to be applied. The present invention is useful for improving the spreading and wetting properties of aqueous mixtures containing powders, liquid droplets in emulsified or non-emulsified form and aqueous solutions of soluble agricultural pesticide materials. The present invention is useful wherever improved wetting properties of an agricultural pesticide is required. The present invention can be useful for improving the spreadability and wetting properties of aqueous mixtures containing both natural or synthetic pesticide materials including biological materials.

The following list comprises agricultural pesticidal materials, wetting properties of whose aqueous mixtures can be improved by inclusion of an aliphatic glycoside and fatty alcohol in the mixture. For simplicity, the agricultural pesticidal materials are listed by their common names.

The wetting ability of aqueous mixtures containing the following fungicidal materials can be improved by including an aliphatic glycoside and fatty alcohol in an aqueous mixture containing the fungicides. Fungicides include Streptomycin, Fosetyl-Al, Metalaxyl, Thiram, Thiabendazole, Propiconazol, Propamocarb-Hydrochloride, Triadimefon, Triadimenol, Benomyl, Copper Hydroxide, Dicloran, Chlorothalonil, TCMTB, Ferbam, Iprodione, Thiophanate, Copper Oxychloride Sulfate, Copper Ammonium Complex, Copper Oxychloride, Zinc Coposil, Basic Copper Sulfate, Chlorothalonil, Chloroneb, Mancozeb, Fentin Hydroxide, Anilazine, Triforine, Thiophanate-Methyl, Dinocap, Calcium Polysufide, Dodemorph Acetate, Terramycin, Copper Oxide, Propiconazol, Vinclozolin, Piperalin, Oxycarboxin, Myclobutanil, Fernabimol, Ethoxyquin, PCNB, Etridiazol, Metham, Carboxin.

The aliphatic glycoside-fatty alcohol compositions are also useful form improving the wetting properties of aqueous mixtures of herbicides such as Atrazine, Nicosulfuron, Fenoxaprop-Ethyl, Glyphosate, Naptalan, Metsulfuron-methyl, Amino Triazole, Diethatyl-Ethyl, Endothal, Simazine, Imazapyr, Imazamethabenz-Methyl, Quizalofop-Ethyl, Asulam, Triallate, Difenzoquat, Benefin, Dicamba, Bentazon, Primisulfuron-methyl, Phenmadipham, Desmedipham, Bensulide, Cyanazine, Acifluorfen-Sodium, Thiobencarb, Bromoxynil, 2,4-DB, Cama, Prometryne, Dichlorbenil, Chlorimuron-Ethyl, Lactofen, Clomazone, Floumeturon, Chlorothal, Napropamide, Metolachlor, Mefluidide, EPTC, Ametryne, Norflurazon, Tribenuron-methyl, Fluaziprop-Butyl, Isoxaben, Triclopyr, Butylate, Chlorsulfuron, Oxyfluorfen, Paraquat, Tebuthiuron, Thifensulfuron-Methyl, Diclofop-Methyl, Bromacil, Imazaquin, Diuron, Pronamide, Fosamine, Alachlor, Metribuzin, Bensulfuron-Methyl, Clopyralid, Linuron, Cacodylic Acid, Ethofumesate, Molinate, Sulfometuronmethyl, Isopropalin, Sethoxydim, Prometone, Methazole, Pendimethalin, Imazethapyr, Pyrazon, Propachlor, Fomesafen, Vernolate, Cycloate, Oxadiazon, Terbacil, Ethalfuralin, Fluridone, Propanil, Oryzalin, MCPB, Pebulate, Picloram, Trifuralin, Siduron, Hexazinone.

The mixture of aliphatic glycoside with fatty alcohol is also useful for improving the wetting and spreading properties of aqueous mixtures containing insecticides such as Temephos, Pirimiphos-Methyl, Avermectin B, Methoprene, Permethrin, Hydramethylnon, Cypermethrin, Clofentezine, Esfenvalerate, Propoxur, Fenthion, Cyflothrin, Nicotine Sulfate, Sulprofos, Bifenthrin, Trimethacarb, Formetanate, Gossyplure, Crotoxyphos, Cyromazine, Coumaphos, Propargite, Terbufos, Profenofos, Dimethoate, Malathion, Dichlorovos, Metaldehyde, Resmethrin, Disulfoton, Naled, Diflurenzuron, Trichlorfon, Chlorpyrifos, Fonofos, Bendiocarb, Tefluthrin, Carbofuran, Lindane, Azinophos-Methyl, Phosmet, Cyhalothrin, Dinocap, Dicofol, Diazinon, Sodium Fluoaluminate, Methomyl, Thiodicarb, Fenoxycarb, Fluvalinate, Methiocarb, Oxydemeton-Methyl, Amitraz, Ethoprophos, Methamidophos, Oxythioquinox, Fenamiphos, Isofenphos, Acephate, Dienochlor, Mevinphos, Fenvalerate, Tetrachlorvinphos, Chlorpyrifos-Methyl, Rayanocide, Propetamphos, Tralometrin, Metham-NA Carbaryl, Methidathion, Fenpropathrin, Aldicarb, Phorate, Endosulfan, Isazofos, Hexakis, Sabadilla, Oxamyl.

The inclusion of a mixture of an aliphatic glycoside and fatty alcohol in an agricultural pesticide material aids in improving the wetting and penetration properties of the mixture. The mixture of the aliphatic glycoside and the fatty alcohol can be included in the concentrate which is diluted for field application or can be added to the agricultural pesticide material in its diluted form for field application. In either method, the mixture of the alkyl glycoside and fatty alcohol substantially improves the ability of the aqueous mixture to wet substrates with which it comes in contact. The substrates can be the ground, plant parts such as roots or leaves, or even the outer surfaces of plant pests.

The mixture of the aliphatic glycoside and fatty alcohol can be added to emulsions, suspensions or solutions of the pesticidal material and water. The mixture of the aliphatic glycoside and the fatty alcohol are particularly useful for addition to solutions such as glyphosate which has a large contact angle between a waxy substrate and the water solution of the composition.

The present invention is not limited to the agricultural pesticides listed above but is applicable in general to improvement in wetting, spreading and plant penetration of aqueous mixtures in general and agricultural pesticide formulations in particular.

The mixture of aliphatic glycoside and fatty alcohol can also be incorporated in nitrogenous fertilizer containing solutions and nitrogenous fertilizer solution containing agricultural pesticide compositions.

The mixture of aliphatic glycoside and fatty alcohol is shown to improve the wetting of oily or waxy surfaces. The mixture can be incorporated into mixtures which are intended to remove oily and waxy materials from substrates. The mixture can be included in hard surface cleaners, scouring agents and the like where oily or waxy materials must be penetrated and removed from the substrate. The mixture of the aliphatic glycoside and fatty alcohol is particularly useful in improving the wetting ability of compositions containing caustic materials such as sodium hydroxide, potassium hydroxide and the like.

We claim:

1. In a method, wherein a substrate is coated with an aqueous composition comprising a material to be coated on the substrate, the improvement which comprises: including in the aqueous composition a wetting increasing effective amount of a mixture of an aliphatic glycoside of the formula $$RO(\underset{\displaystyle R'}{\underset{|}{CH}}-CH_2O)_yG_x$$

and from about 2% to about 20% by weight of a fatty alcohol, based on the amount of the glycoside and alcohol, the fatty alcohol having from about 7 to about 20 carbon atoms, wherein RO is the residue of a fatty alcohol containing from about 7 to about 18 carbon atoms, R' is H, $CH_3$ or $CH_3CH_2$, G is the residue of a reducing saccharide, y is an average number of from about 0 to about 5, and x is an average degree of polymerization of from 1 to about 4, relative to the aqueous composition without the mixture.

2. A method of claim 1 wherein the material which is to be coated on the substrate is an agricultural pesticide and the substrate is the foliage of a plant.

3. A method of claim 1 wherein R is an aliphatic group containing from about 8 to about 16 carbon atoms, y is O, G is a glucose residue and x is a number of from about 1 to about 3.

4. A method of claim 3 wherein x is a number of from 1 to about 1.15 and R is an aliphatic group containing from 8 to 12 carbon atoms.

5. A method of claim 3 wherein the aliphatic glucoside contains at least about 90% by weight of a monoglucoside.

6. A method of claim 4 wherein x is a number of from 1 to about 1.05.

7. A method of claim 5 wherein R is an alkyl group containing from 8 to 12 carbon atoms.

8. A method of claim 1 wherein the aqueous mixture additionally comprises a glyphosate salt.

9. A method of claim 1 wherein the mixture of the aliphatic glycoside and alcohol contains from about 2% by weight to about 15% by weight of the fatty alcohol.

10. A method of claim 9 wherein the alcohol contains from 8 to 16 carbon atoms.

11. A method of claim 10 wherein x is a number of from 1 to 1.15 and RO is a residue of a fatty alcohol containing from 8 to 12 carbon atoms.

12. A method of claim 11 wherein x is a number of from 1 to 1.05 and RO is a residue of a fatty alcohol containing from 8 to about 10 carbon atoms.

13. A method of claim 11 wherein the composition further comprises glyphosate isopropylamine salt.

14. A method of claim 1 wherein the material to be coated on the substrate is an agricultural pesticide material.

15. A method of claim 14 wherein R is a $C_8$ to $C_{10}$aliphatic group, x is a number from 1 to 1.15 and the alcohol is a fatty alcohol containing from 8 to 16 carbon atoms.

16. A method of claim 15 wherein x is a number of from 1 to 1.05 and the fatty alcohol contains from 8 to 14 carbon atoms.

17. A method of claim 15 wherein the mixture of aliphatic glycoside and fatty alcohol contain from 2 to about 15% by weight fatty alcohol.

18. A method of claim 17 wherein the glycoside comprises a glucoside.

19. A method of claim 16 wherein the glycoside comprises a glucoside.

20. A method of claim 11 wherein the glycoside comprises a glucoside.

21. A method of claim 12 wherein the glycoside comprises a glucoside.

22. A method of claim 1 wherein the material to be coated on the substrate is an alkaline cleaning composition.

23. A method of claim 1 wherein the material to be coated on the substrate is a nitrogenous fertilizer solution.

24. A method of claim 23 wherein the nitrogenous fertilizer solution comprises an agricultural pesticide composition.

* * * * *